(12) United States Patent
Chow et al.

(10) Patent No.: US 10,835,259 B2
(45) Date of Patent: Nov. 17, 2020

(54) OCCLUSIVE MEDICAL DEVICE SYSTEM

(71) Applicant: BOSTON SCIENTIFIC SCIMED, INC., Maple Grove, MN (US)

(72) Inventors: Hoi Ki Ricky Chow, New Brighton, MN (US); David B. Morris, Anoka, MN (US); John D. Kroeger, Mounds View, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 319 days.

(21) Appl. No.: 15/918,513

(22) Filed: Mar. 12, 2018

(65) Prior Publication Data

US 2018/0256171 A1 Sep. 13, 2018

Related U.S. Application Data

(60) Provisional application No. 62/470,584, filed on Mar. 13, 2017.

(51) Int. Cl.
*A61B 17/12* (2006.01)
*A61B 17/00* (2006.01)
*A61B 90/00* (2016.01)

(52) U.S. Cl.
CPC .... *A61B 17/12145* (2013.01); *A61B 17/1215* (2013.01); *A61B 17/12109* (2013.01);
(Continued)

(58) Field of Classification Search
CPC ........ A61B 17/12022; A61B 17/12109; A61B 17/12113; A61B 17/1214;
(Continued)

(56) References Cited

U.S. PATENT DOCUMENTS 3,342,179 A 9/1967 Ellmann
5,117,839 A 6/1992 Dance
(Continued)

FOREIGN PATENT DOCUMENTS

EP 2777542 A2 9/2014
EP 2777545 A2 9/2014
(Continued)

OTHER PUBLICATIONS

International Search Report & Written Opinion dated Jun. 15, 2018 for International Application No. PCT/US2018/021978.
(Continued)

*Primary Examiner* — Robert A Lynch
(74) *Attorney, Agent, or Firm* — Seager, Tufte & Wickhem LLP

(57) ABSTRACT

An occlusive medical device system may include an elongate shaft having a distal strain relief portion and a lumen extending longitudinally through the elongate shaft, the elongate shaft including a plurality of retaining arms extending distally from the distal strain relief portion; an occlusive medical device including a proximal mounting portion fixed to an expandable occlusive element; and a release wire disposed within the lumen of the elongate shaft. The plurality of retaining arms may extend into the proximal mounting portion. The release wire may be configured to engage the plurality of retaining arms in a distal engagement position, thereby urging the plurality of retaining arms radially outward into releasable engagement with the proximal mounting portion. When the release wire is in a proximal released position, the plurality of retaining arms is deflectable radially inward to disengage from the proximal mounting portion.

19 Claims, 15 Drawing Sheets

(52) U.S. Cl.
CPC ............... *A61B 17/12159* (2013.01); *A61B 2017/00867* (2013.01); *A61B 2017/12054* (2013.01); *A61B 2090/3966* (2016.02)

(58) Field of Classification Search
CPC .......... A61B 17/12145; A61B 17/1215; A61B 17/12154; A61B 17/12159; A61B 17/12168; A61B 17/12172; A61B 17/12177; A61B 2017/1205; A61B 2017/12054
See application file for complete search history.

(56) References Cited

U.S. PATENT DOCUMENTS

| | | | |
|---|---|---|---|
| 5,234,437 | A | 8/1993 | Sepetka |
| 5,250,071 | A | 10/1993 | Palermo |
| 5,282,478 | A | 2/1994 | Fleischhaker, Jr. et al. |
| 5,304,195 | A | 4/1994 | Twyford, Jr. et al. |
| 5,546,958 | A | 8/1996 | Thorud et al. |
| RE37,117 | E | 3/2001 | Palermo |
| 6,277,125 | B1 | 8/2001 | Barry et al. |
| 6,491,646 | B1 | 12/2002 | Blackledge |
| 7,044,134 | B2 | 5/2006 | Khairkhahan et al. |
| 9,198,670 | B2 | 12/2015 | Hewitt et al. |
| 9,307,999 | B2 | 4/2016 | Li et al. |
| 9,468,442 | B2 | 10/2016 | Huynh et al. |
| 2007/0135826 | A1 | 6/2007 | Zaver et al. |
| 2007/0282373 | A1 | 12/2007 | Ashby et al. |
| 2008/0109059 | A1 | 5/2008 | Gordon et al. |
| 2008/0119891 | A1 | 5/2008 | Miles et al. |
| 2008/0300616 | A1 | 12/2008 | Que et al. |
| 2009/0043331 | A1 | 2/2009 | Buiser et al. |
| 2009/0163934 | A1 | 6/2009 | Raschdorf, Jr. et al. |
| 2009/0177261 | A1 | 7/2009 | Teoh et al. |
| 2010/0121350 | A1 | 5/2010 | Mirigian |
| 2012/0046687 | A1 | 2/2012 | Trommeter et al. |
| 2012/0316597 | A1* | 12/2012 | Fitz ............... A61B 17/12031 606/194 |
| 2014/0058434 | A1 | 2/2014 | Jones et al. |
| 2014/0058435 | A1 | 2/2014 | Jones et al. |
| 2014/0277078 | A1* | 9/2014 | Slazas ............ A61B 17/1214 606/200 |
| 2015/0272589 | A1 | 10/2015 | Lorenzo |
| 2015/0327868 | A1 | 11/2015 | Islak et al. |
| 2015/0335333 | A1 | 11/2015 | Jones et al. |
| 2015/0342611 | A1 | 12/2015 | Leopold et al. |
| 2016/0030052 | A1 | 2/2016 | Cragg et al. |
| 2016/0113657 | A1* | 4/2016 | Mathis ........... A61B 17/12145 606/157 |
| 2016/0166257 | A1 | 6/2016 | Allen et al. |
| 2016/0192942 | A1* | 7/2016 | Strauss ........... A61B 17/12113 606/200 |
| 2016/0228123 | A1 | 8/2016 | Anderson et al. |
| 2016/0228124 | A1 | 8/2016 | Trommeter et al. |
| 2016/0228128 | A1 | 8/2016 | Connolly |
| 2016/0317274 | A1 | 11/2016 | Liu et al. |
| 2018/0133435 | A1 | 5/2018 | Pederson, Jr. et al. |

FOREIGN PATENT DOCUMENTS

| | | |
|---|---|---|
| JP | 2016537134 A | 12/2016 |
| WO | 0232496 A1 | 4/2002 |
| WO | 2007070797 A2 | 6/2007 |
| WO | 2010030993 A1 | 3/2010 |

OTHER PUBLICATIONS

PCT Application No. PCT/US2017/061779 International Search Report and Written Opinion, dated Feb. 26, 2018.

* cited by examiner

OCCLUSIVE MEDICAL DEVICE SYSTEM

CROSS-REFERENCE TO RELATED APPLICATIONS

This application claims the benefit of priority under 35 U.S.C. § 119 to U.S. Provisional Application Ser. No. 62/470,584, filed Mar. 13, 2017, the entirety of which is incorporated herein by reference.

TECHNICAL FIELD

The present disclosure pertains to medical devices, and methods for manufacturing and/or using medical devices. More particularly, the present disclosure pertains to a vascular occlusion device and/or apparatus and methods of manufacture therefor.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and/or using medical devices.

SUMMARY

In a first aspect, an occlusive medical device system may comprise an elongate shaft having a proximal end, a distal strain relief portion, and a lumen extending longitudinally through the elongate shaft, the elongate shaft further comprising a plurality of retaining arms extending distally from the distal strain relief portion. The occlusive medical device system may comprise an occlusive medical device configured to occlude fluid flow through a vessel lumen, the occlusive medical device including a proximal mounting portion fixed to an expandable occlusive element. The occlusive medical device system may comprise a release wire disposed within the lumen of the elongate shaft and axially translatable between a distal engagement position and a proximal released position. The plurality of retaining arms may extend into the proximal mounting portion. The release wire may be configured to engage the plurality of retaining arms in the distal engagement position, thereby urging the plurality of retaining arms radially outward into releasable engagement with the proximal mounting portion of the occlusive medical device. When the release wire is in the proximal released position, the plurality of retaining arms is deflectable radially inward to disengage from the proximal mounting portion.

In addition or alternatively, and in a second aspect, the distal strain relief portion includes a plurality of micromachined or laser cuts extending at an angle to a longitudinal axis of the elongate shaft from an outer surface of the elongate shaft through to the lumen extending through the elongate shaft.

In addition or alternatively, and in a third aspect, the plurality of micromachined or laser cuts extend perpendicular to the longitudinal axis of the elongate shaft.

In addition or alternatively, and in a fourth aspect, the proximal mounting portion includes a plurality of apertures configured to engage the plurality of retaining arms when the release wire is in the distal engagement position.

In addition or alternatively, and in a fifth aspect, each of the plurality of retaining arms includes a protrusion extending radially outward from an outer surface of the retaining arm.

In addition or alternatively, and in a sixth aspect, each of the protrusions of the plurality of retaining arms engages one of the plurality of apertures of the proximal mounting portion when the release wire is in the distal engagement position.

In addition or alternatively, and in a seventh aspect, an occlusive medical device system may comprise an elongate shaft having a proximal end, a distal strain relief portion, and a lumen extending longitudinally through the elongate shaft, the elongate shaft further comprising a plurality of retaining arms extending distally from the distal strain relief portion, each retaining arm having a protrusion proximate a distal end thereof and extending radially outward from an outwardly-facing surface of the retaining arm. The occlusive medical device system may comprise an occlusive medical device configured to occlude fluid flow through a vessel lumen, the occlusive medical device including a proximal tubular mounting portion fixed to an expandable occlusive element, the proximal tubular mounting portion including a lumen extending longitudinally through the proximal tubular mounting portion and a ridge extending radially inward from an inwardly-facing surface of the proximal tubular mounting portion proximate a proximal end of the proximal tubular mounting portion. The occlusive medical device system may comprise a release wire disposed within the lumen of the elongate shaft and axially translatable between a distal engagement position and a proximal released position. The plurality of retaining arms may extend into the proximal tubular mounting portion. The release wire may be configured to engage the plurality of retaining arms in the distal engagement position, thereby urging the plurality of retaining arms radially outward such that proximal axial translation of the elongate shaft relative to the proximal tubular mounting portion is prevented. When the release wire is in the proximal released position, the plurality of retaining arms is deflectable radially inward such that proximal axial translation of the elongate shaft relative to the proximal tubular mounting portion is permitted.

In addition or alternatively, and in an eighth aspect, the ridge is integrally formed with the proximal tubular mounting portion.

In addition or alternatively, and in a ninth aspect, the ridge is formed as a part of a tubular ring fixedly attached to a proximal end of the proximal tubular mounting portion.

In addition or alternatively, and in a tenth aspect, the ridge defines a proximal aperture having a diameter less than a diameter of the lumen of the proximal tubular mounting portion.

In addition or alternatively, and in an eleventh aspect, the diameter of the proximal aperture is less than a maximum outer extent of the protrusions of the plurality of retaining arms when the release wire is in the distal engagement position.

In addition or alternatively, and in a twelfth aspect, the occlusive medical device includes a radiopaque insert disposed within the lumen of the proximal tubular mounting portion.

In addition or alternatively, and in a thirteenth aspect, the elongate shaft is axially slidable within the proximal tubular mounting portion.

In addition or alternatively, and in a fourteenth aspect, advancing the elongate shaft distally urges the distal ends of the plurality of retaining arms into contact with the radiopaque insert.

In addition or alternatively, and in a fifteenth aspect, when the release wire is in the distal engagement position, withdrawing the elongate shaft proximally urges the protrusions of the plurality of retaining arms into contact with the ridge.

In addition or alternatively, and in a sixteenth aspect, an occlusive medical device system may comprise an elongate shaft having a proximal end, a distal strain relief portion, and a lumen extending longitudinally through the elongate shaft, the elongate shaft further comprising a plurality of retaining arms extending distally from the distal strain relief portion. The occlusive medical device system may comprise an occlusive medical device configured to occlude fluid flow through a vessel lumen, the occlusive medical device including a proximal mounting portion fixed to an expandable occlusive element comprising a support frame and an occlusive membrane attached to the support frame. The occlusive medical device system may comprise a release wire disposed within the lumen of the elongate shaft and axially translatable between a distal engagement position and a proximal released position. The plurality of retaining arms may extend into the proximal mounting portion. The release wire may be configured to engage the plurality of retaining arms in the distal engagement position, thereby urging the plurality of retaining arms radially outward into releasable engagement with the proximal mounting portion of the occlusive medical device. When the release wire is in the proximal released position, the plurality of retaining arms is deflectable radially inward to disengage from the proximal mounting portion.

In addition or alternatively, and in a seventeenth aspect, the occlusive medical device includes a lumen extending longitudinally through the proximal mounting portion and a radiopaque marker fixedly secured within a distal end of the lumen extending longitudinally through the proximal mounting portion.

In addition or alternatively, and in an eighteenth aspect, the proximal mounting portion includes a plurality of protrusions extending radially inward into the lumen extending longitudinally through the proximal mounting portion.

In addition or alternatively, and in a nineteenth aspect, each of the plurality of retaining arms includes an aperture configured to engage one of the plurality of protrusions when the release wire is in the distal engagement position.

In addition or alternatively, and in a twentieth aspect, the occlusive medical device system may comprise a securement member having a proximal portion fixedly attached to a proximal end of the release wire and a distal portion fixedly attached to a proximal end of the elongate shaft. The securement member may be configured to prevent axial translation of the release wire relative to the elongate shaft prior to disengagement of the proximal portion of the securement member from the distal portion of the securement member and permit axial translation of the release wire relative to the elongate shaft after disengagement of the proximal portion of the securement member from the distal portion of the securement member.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
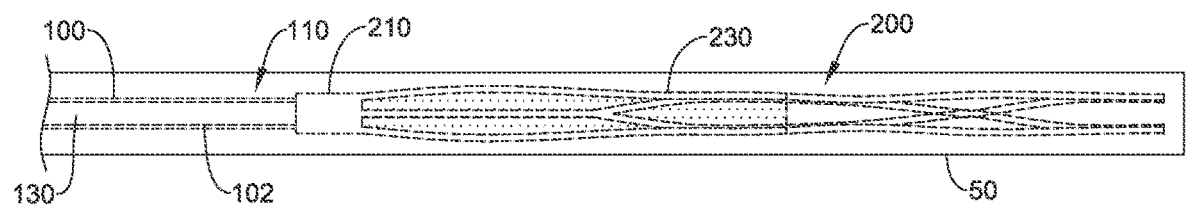
FIG. 1 illustrates an example occlusive medical device system including an occlusive medical device in a delivery configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

Figure 2:
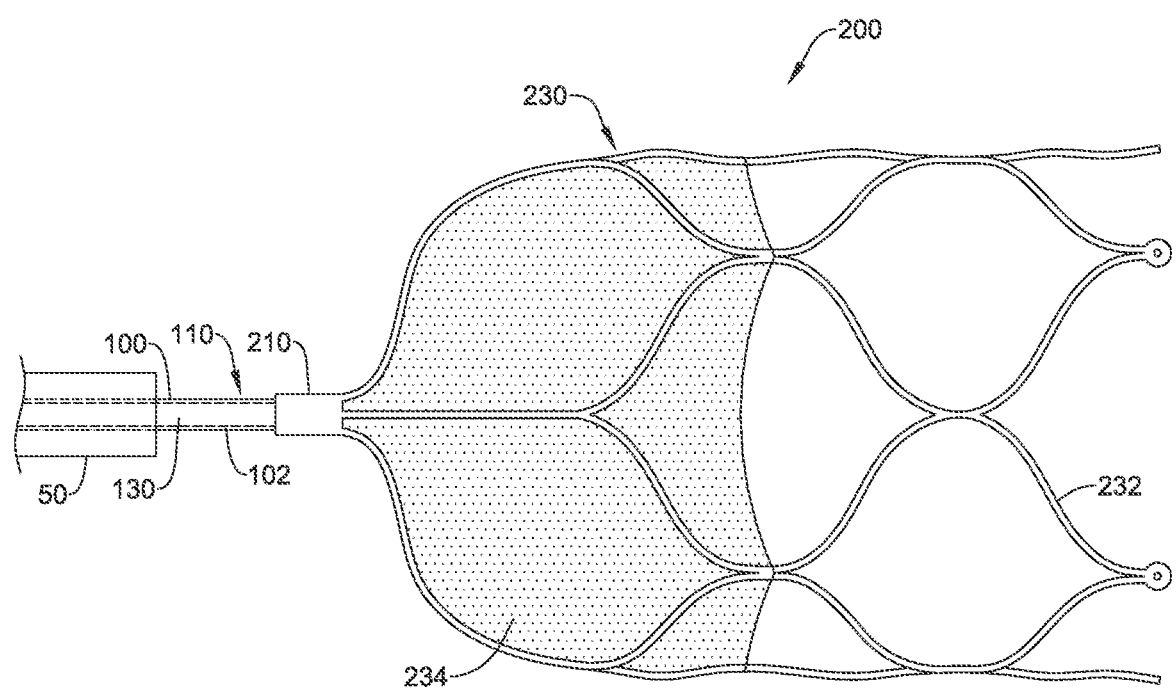
FIG. 2 illustrates the occlusive medical device system including the occlusive medical device in an expanded configuration.

FIGS. 1 and 2 illustrate an example occlusive medical device system. Certain details of various elements of the occlusive medical device system are described in greater detail below with reference to FIGS. 3-13. The occlusive medical device system may comprise a delivery sheath 50 having a lumen extending through the delivery sheath 50. The occlusive medical device system may comprise an elongate shaft 100 slidably disposed within the lumen of the delivery sheath 50. The elongate shaft 100 may include a proximal end, a distal strain relief portion 110 opposite the proximal end, and a lumen 102 extending longitudinally through the elongate shaft 100 along a longitudinal axis of the elongate shaft 100. Additionally, the occlusive medical device system may comprise a release wire 130 slidably disposed within the lumen 102 of the elongate shaft 100 and axially translatable between a distal engagement position (e.g., FIG. 3) and a proximal released position (e.g., FIG. 7), for reasons that will become apparent. In some embodiments, a proximal portion and/or proximal end of the release wire 130 may be releasably secured to the proximal end of the elongate shaft 100, for example, using (but not limited to) a perforated polymer joint, a dissimilar polymer joint, a frangible joint, etc. Some suitable but non-limiting materials for the delivery sheath 50, the elongate shaft 100, and/or the release wire 130, for example metallic materials, polymer materials, composite materials, etc., are described below.

The occlusive medical device system may comprise an occlusive medical device 200 configured to occlude fluid and/or blood flow through a vessel lumen (e.g., an artery, etc.). The occlusive medical device 200 may include a proximal tubular mounting portion 210 fixed to, fixedly attached to, and/or integrally formed with an expandable occlusive element 230. The occlusive medical device 200 may have and/or define a longitudinal axis extending from the proximal tubular mounting portion 210 through and/or along the expandable occlusive element 230. In some embodiments, at least a portion of the elongate shaft 100 may extend into and/or releasably engage with the proximal tubular mounting portion 210 of the occlusive medical device 200. In some embodiments, the distal strain relief portion 110 of the elongate shaft 100 may provide flexibility and/or more flexibility to the elongate shaft 100 adjacent the occlusive medical device 200, thereby preventing kinking, breakage, etc. of the elongate shaft 100 and/or the release wire 130. The occlusive medical device 200 and/or the expandable occlusive element 230 may be radially expandable and/or longitudinally foreshortenable from a delivery configuration (e.g., FIG. 1) to an expanded configuration (e.g., FIG. 2). The expandable occlusive element 230 may comprise a support frame 232 and an occlusive membrane 234 fixedly attached to, encapsulating, and/or surrounding at least a portion of the support frame 232. Alternatively, the occlusive medical device 200 may be and/or include a vascular plug, an embolic coil, or other suitable occlusive medical device.

In some embodiments, the occlusive medical device 200 and/or the expandable occlusive element 230 may be disposed within a distal portion of the delivery sheath 50 in the delivery configuration, as seen in FIG. 1. After advancing and/or navigating the occlusive medical device 200 to a target site or area of interest, the elongate shaft 100 and/or the occlusive medical device 200 may be advanced distally out of the delivery sheath 50, and/or the delivery sheath 50 may be retracted proximally as the elongate shaft 100 and/or the occlusive medical device 200 is held in a fixed position, (e.g., the elongate shaft 100 and/or the occlusive medical device 200 may be translated longitudinally relative to the delivery sheath 50) to expose the occlusive medical device 200. In at least some embodiments, the support frame 232 may be formed from a self-expanding material configured to automatically expand toward and/or to the expanded configuration when unconstrained (e.g., the support frame 232 may be configured to shift from the delivery configuration to the expanded configuration), as seen in FIG. 2. In some embodiments, the support frame 232 may be formed from a shape memory material or other material configured with a "trigger" (e.g., temperature, electrical current, etc.) such that the support frame 232 may remain in the delivery configuration until the support frame 232 is "activated", at which time the support frame 232 may shift to the expanded configuration. Other embodiments are also envisioned which may utilize mechanical expansion and/or a supporting expansion member to shift the occlusive medical device 200, the expandable occlusive element 230, and/or the support frame 232 from the delivery configuration to the expanded configuration.

In some embodiments, the expandable occlusive element 230 and/or the support frame 232 may include and/or comprise at least one strut, support, and/or member. In some embodiments, the expandable occlusive element 230 and/or the support frame 232 may include and/or comprise a plurality of struts, supports, and/or members interconnected, joined together, and/or integrally formed with each other. In at least some embodiments, the expandable occlusive element 230 and/or the support frame 232 may include a generally closed first end proximate the proximal tubular mounting portion 210 of the occlusive medical device 200 and a generally open second end opposite the generally closed first end, wherein the expandable occlusive element 230 and/or the support frame 232 expands radially outward from and opens away from the proximal tubular mounting portion 210 of the occlusive medical device 200. In some embodiments, the expandable occlusive element 230 and/or the support frame 232 may include a generally closed first end proximate the proximal tubular mounting portion 210 of the occlusive medical device 200 and a generally closed second end opposite the generally closed first end, wherein a middle portion of the expandable occlusive element 230 and/or the support frame 232 expands radially outward from and/or between the generally closed first end and the generally closed second end. The expandable occlusive element 230 and/or the support frame 232 may have and/or define a longitudinal length along a longitudinal axis of the occlusive medical device 200. Some suitable but non-limiting materials for the expandable occlusive element 230 and/or the support frame 232, for example metallic materials, polymer materials, composite materials, etc., are described below.

As mentioned above, the occlusive membrane 234 may be fixedly attached to, encapsulate, and/or surround at least a portion of the support frame 232. In some embodiments, the occlusive membrane 234 may be disposed on and/or attached to an inside surface of the expandable occlusive element 230 and/or the support frame 232, an outside surface of the expandable occlusive element 230 and/or the support frame 232, and/or may extend between individual struts, supports, and/or members of the expandable occlusive element 230 and/or the support frame 232. In some embodiments, the occlusive membrane 234 may include a generally closed first end proximate the proximal tubular mounting portion 210 of the occlusive medical device 200 and a generally open second end opposite the generally closed first end. In some embodiments, the occlusive membrane 234 may include a generally closed first end proximate the proximal tubular mounting portion 210 of the occlusive medical device 200 and a generally closed second end opposite the generally closed first end. In some embodiments, the generally closed first end of the occlusive membrane 234 may be disposed at and/or may be fixedly attached to the proximal tubular mounting portion 210 of the occlusive medical device 200. In some embodiments, the generally closed first end of the occlusive membrane 234 may be disposed distal of the proximal tubular mounting portion 210 of the occlusive medical device 200. In some embodiments, the occlusive membrane 234 may extend along a portion of the longitudinal length of the expandable occlusive element 230 and/or the support frame 232. For example, the second end of the occlusive membrane 234 may be disposed between the first end of the expandable occlusive element 230 and/or the support frame 232 and the second end of the expandable occlusive element 230 and/or the support frame 232. In some embodiments, the second end of the occlusive membrane 234 may be substantially straight and/or arranged in a planar manner normal to the longitudinal axis of the occlusive medical device 200. In some embodiments, the second end of the occlusive membrane 234 may be substantially scalloped and/or have a variable longitudinal length along and/or relative to the longitudinal axis of the occlusive medical device 200. In some embodiments, the occlusive membrane 234 may extend along the entire longitudinal length of the expandable occlusive element 230 and/or the support frame 232.

In some embodiments, the occlusive membrane 234 may be substantially non-porous and/or impermeable to fluid. For example, in some embodiments, blood or other fluid(s) may be unable to pass through the occlusive membrane 234. As such, when the occlusive medical device 200 and/or the expandable occlusive element 230 is deployed within the vessel lumen (e.g., an artery, etc.) in the expanded configuration, the expandable occlusive element 230, the support frame 232, and/or the occlusive membrane 234 may extend across the vessel lumen and substantially and/or completely block and/or occlude fluid and/or blood flow through the vessel lumen. In some embodiments, the occlusive membrane 234 may include and/or be formed from a knitted, woven, and/or porous material having an impermeable coating and/or layer of material (e.g., polymeric material, etc.) formed thereon and/or thereover. In some embodiments, the occlusive membrane 234 may include and/or be formed from a knitted, woven, and/or porous material where blood quickly coagulates to form an impermeable barrier. Some suitable but non-limiting materials for the occlusive membrane 234, for example metallic materials, polymer materials, composite materials, textile materials, etc., are described below.

Figure 3:
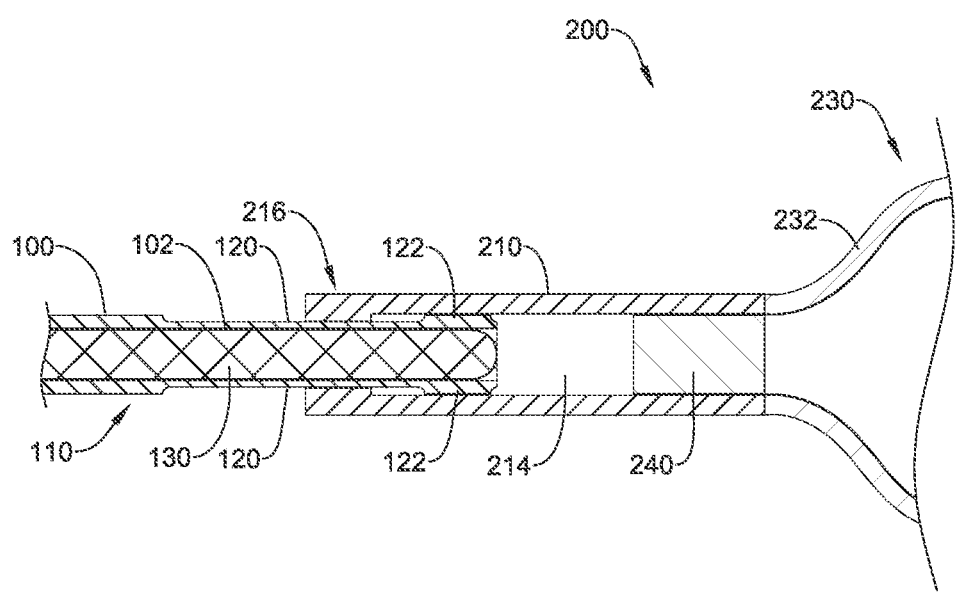
FIG. 3 illustrates an example attachment mechanism of the occlusive medical device system.
Figure 4:
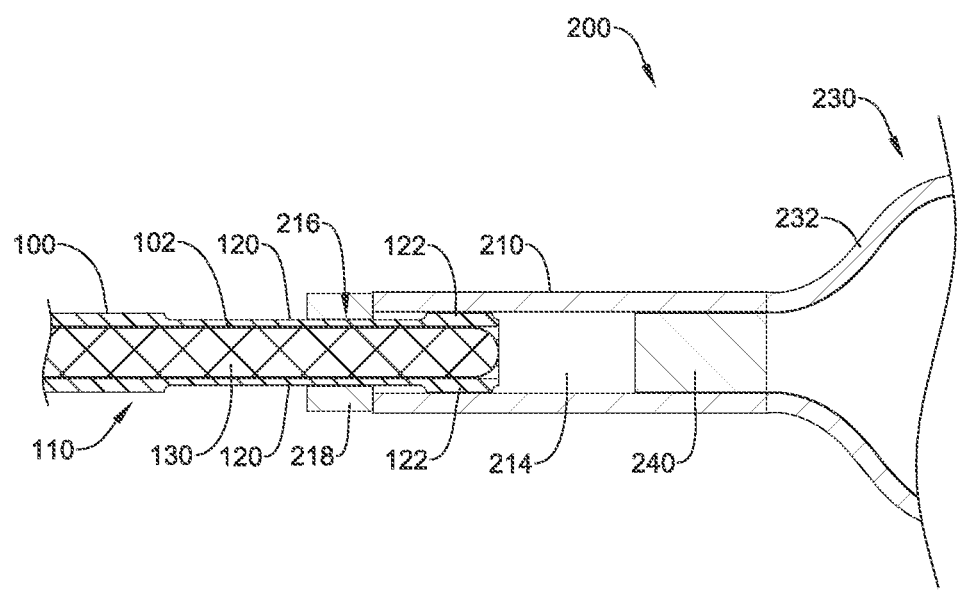
FIG. 4 illustrates an alternative configuration of the attachment mechanism of FIG. 3.

FIGS. 3 and 4 illustrate an example attachment mechanism of the occlusive medical device system. As mentioned above, the elongate shaft 100 may include a proximal end, a distal strain relief portion 110 opposite the proximal end, and a lumen 102 extending longitudinally through the elongate shaft 100. The elongate shaft 100 may further comprise and/or include a plurality of retaining arms 120 extending distally from the distal strain relief portion 110, the plurality of retaining arms 120 each having a distal end opposite the distal strain relief portion 110. In some embodiments, the plurality of retaining arms 120 may be biased radially inward. In some embodiments, the plurality of retaining arms 120 may be self-biased radially inward. In some embodiments, the plurality of retaining arms 120 may be configured to deflect radially inward when unconstrained and/or when not biased radially outwardly by the release wire 130 as described herein. In some embodiments, the plurality of retaining arms 120 may comprise two retaining arms, three retaining arms, four retaining arms, or another suitable number of retaining arms.

In some embodiments, the plurality of retaining arms 120 may be arranged circumferentially about the longitudinal axis of the elongate shaft 100. In some embodiments, a longitudinally-extending slot may extend between adjacent retaining arms 120, thereby radially, angularly, and/or circumferentially spacing apart the adjacent retaining arms 120. For example, centerlines (arranged generally parallel to the longitudinal axis of the elongate shaft 100) of each of the plurality of retaining arms 120 may be arranged and/or spaced apart at equal and/or regular radial, angular, and/or circumferential intervals (e.g., 90 degrees apart, 120 degrees apart, etc.) about the longitudinal axis of the elongate shaft 100. Alternatively, in some embodiments, centerlines (arranged generally parallel to the longitudinal axis of the elongate shaft 100) of each of the plurality of retaining arms 120 may be arranged and/or spaced apart at unequal and/or irregular radial, angular, and/or circumferential intervals about the longitudinal axis of the elongate shaft 100, with appropriate changes to the spacing (e.g., size of longitudinally-extending slot, etc.) of the plurality of retaining arms 120 to permit the desired inward deflection of the plurality of retaining arms 120, as described herein. The plurality of retaining arms 120 may be formed and/or made by one or more of a variety of suitable means including, but not limited to, machining, cutting (e.g., laser, water jet, etc.), electro discharge machining, grinding, etc.

Figure 6:
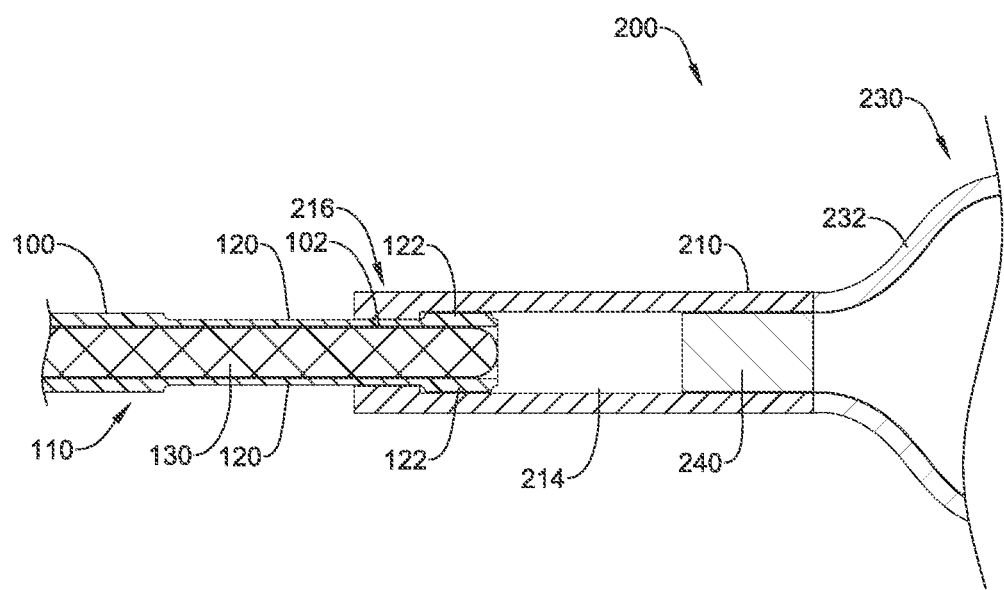

The elongate shaft 100 may include the release wire 130 slidably disposed within the lumen 102 of the elongate shaft 100 and axially translatable between the distal engagement position (e.g., FIGS. 3 and 4) and the proximal released position (e.g., FIG. 6). As seen in the figures, the plurality of retaining arms 120 may extend into a lumen 214 extending longitudinally through the proximal tubular mounting portion 210. The release wire 130 may be configured to engage the plurality of retaining arms 120 in the distal engagement position, thereby urging the plurality of retaining arms 120 radially outward into releasable engagement with the proximal tubular mounting portion 210 of the occlusive medical device 200 such that proximal axial translation of the elongate shaft 100 relative to the proximal tubular mounting portion 210 is prevented. When the release wire 130 is axially translated to and/or disposed in the proximal released position (e.g., FIG. 7), the plurality of retaining arms 120 may deflect radially inward and disengage from the proximal tubular mounting portion 210 such that proximal axial translation of the elongate shaft 100 relative to the proximal tubular mounting portion 210 is permitted. In some embodiments, when the release wire 130 is axially translated to and/or disposed in the proximal released position (e.g., FIG. 7), the plurality of retaining arms 120 may be biased and/or self-biased radially inward and disengage from the proximal tubular mounting portion 210 such that proximal axial translation of the elongate shaft 100 relative to the proximal tubular mounting portion 210 is permitted.

In at least some embodiments, each of the plurality of retaining arms 120 may include a protrusion 122 proximate the distal end thereof and extending radially outward from an outer surface and/or an outwardly-facing surface of the retaining arm 120. In some embodiments, the protrusion 122 on each of the plurality of retaining arms 120 may be urged radially outward into releasable engagement with the proximal tubular mounting portion 210 of the occlusive medical device 200 when the release wire 130 is in the distal engagement position. The protrusion 122 of each of the plurality of retaining arms 120 may be formed on and/or added to its respective retaining arm using one or more suitable means including, but not limited to, adhesive, soldering, welding, grinding, electro discharge machining, etc.

In some embodiments, the proximal tubular mounting portion 210 may include a ridge 216 extending radially inward from an inwardly-facing surface of the proximal tubular mounting portion 210 proximate a proximal end of the lumen 214 and/or the proximal tubular mounting portion 210. In some embodiments, the ridge 216 may be integrally formed with the proximal tubular mounting portion 210, as seen in FIG. 3 for example. In some embodiments, the ridge 216 may be formed as a part of a tubular ring 218 fixedly attached to a proximal end of the proximal tubular mounting portion 210, as seen in FIG. 4 for example. The tubular ring 218 may be fixedly attached to the proximal end of the proximal tubular mounting portion 210 using one or more suitable means, including but not limited to, welding, adhesives, mechanical fasteners, interference fit, etc. In some embodiments, the elongate shaft 100 and/or the plurality of retaining arms 120 may be axially slidable within the lumen 214 of the proximal tubular mounting portion 210.

In some embodiments, the occlusive medical device 200 may include a radiopaque insert 240 disposed within a distal end of the lumen 214 extending longitudinally through the proximal tubular mounting portion 210. In some embodiments, the radiopaque insert 240 may be fixedly and/or permanently secured within the distal end of the lumen 214 extending longitudinally through the proximal tubular mounting portion 210. In some embodiments, the lumen 214 may not extend completely through the proximal tubular mounting portion 210. For example, the distal end of the lumen 214 proximate the expandable occlusive element 230 and/or the support frame 232 may be closed.

Figure 5:
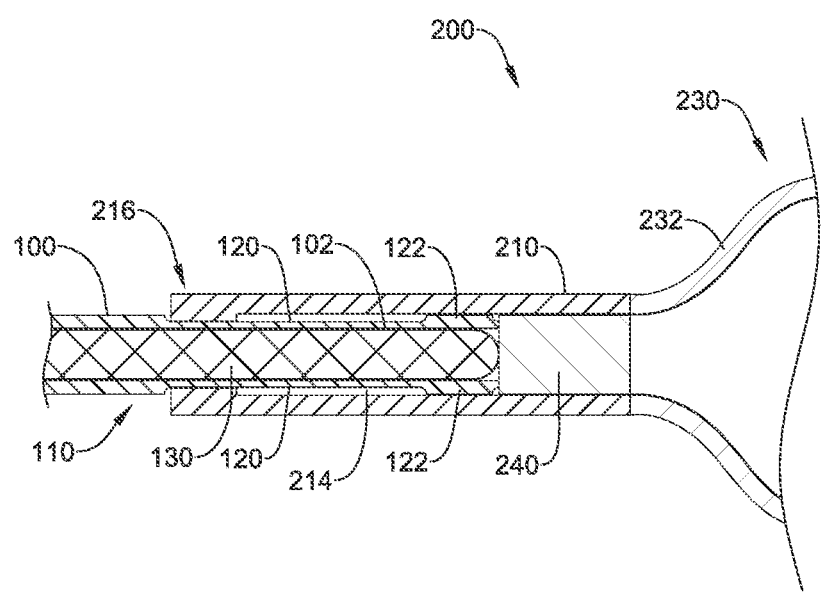
FIGS. 5-7 illustrate example functions of the attachment mechanism(s) of the disclosure.
Figure 7:
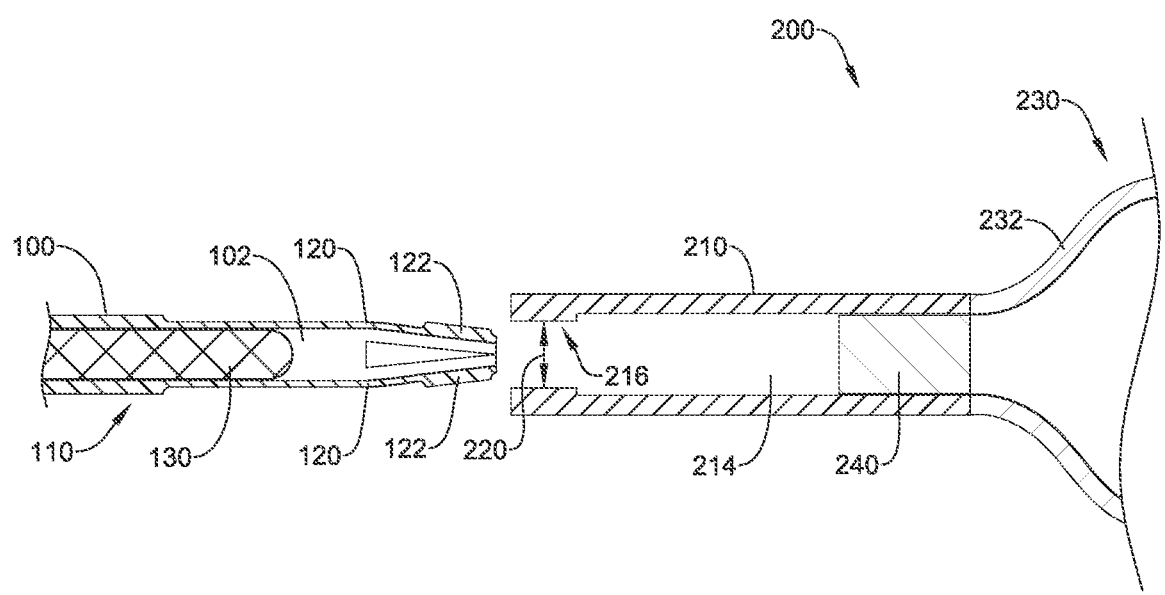

As shown in FIG. 5, advancing the elongate shaft 100 and the release wire 130 disposed in the distal engagement position distally and/or axially translating the elongate shaft 100 and the release wire 130 disposed in the distal engagement position distally within the lumen 214 extending through the proximal tubular mounting portion 210 urges the distal ends of each of the plurality of retaining arms 120 into contact with the radiopaque insert 240 and/or the closed distal end of the lumen 214 (where so configured). Further distal advancement and/or axial translation of the elongate shaft 100 relative to the delivery sheath 50 may advance and/or translate the occlusive medical device 200 distally relative to the delivery sheath 50. In some embodiments, when the release wire 130 is disposed in the distal engagement position, withdrawing the elongate shaft 100 and the release wire 130 proximally urges the protrusion 122 of each of the plurality of retaining arms 120 into contact with a distal face of the ridge 216, as shown in FIG. 6. Withdrawing the release wire 130 axially within the elongate shaft 100 from the distal engagement position to the proximal released position permits the plurality of retaining arms 120 to deflect radially inward and disengage from the proximal tubular mounting portion 210, as shown in FIG. 7. In some embodiments, withdrawing the release wire 130 axially within the elongate shaft 100 from the distal engagement position to the proximal released position permits the plurality of retaining arms 120 to be biased and/or self-biased radially inward and thereby disengage from the proximal tubular mounting portion 210, as shown in FIG. 7. For example, when the retaining arms 120 are deflected and/or biased radially inward they have a diameter less than a proximal aperture 220. As also seen in FIG. 7, the ridge 216 defines the proximal aperture 220 having a diameter less than a diameter of the lumen 214 extending through the proximal tubular mounting portion 210. The diameter of the proximal aperture 220 is also less than a maximum outer extent of the protrusions 122 of the plurality of retaining arms 120 when the release wire 130 is in the distal engagement position. When assembling the attachment mechanism, the plurality of retaining arms 120 are extended through the proximal aperture 220 into the lumen 214 of the proximal tubular mounting portion 210 prior to advancing the release wire 130 to the distal engagement position and into engagement with the plurality of retaining arms 120.

Figure 8:
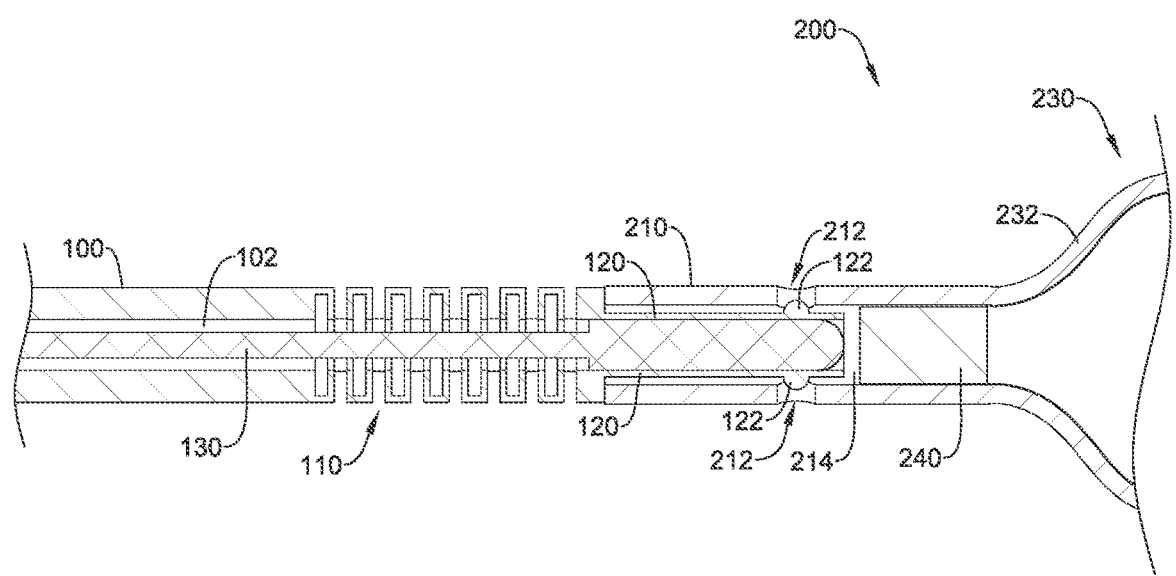
FIGS. 8-9 illustrate an alternative attachment mechanism of the occlusive medical device system.
Figure 9:
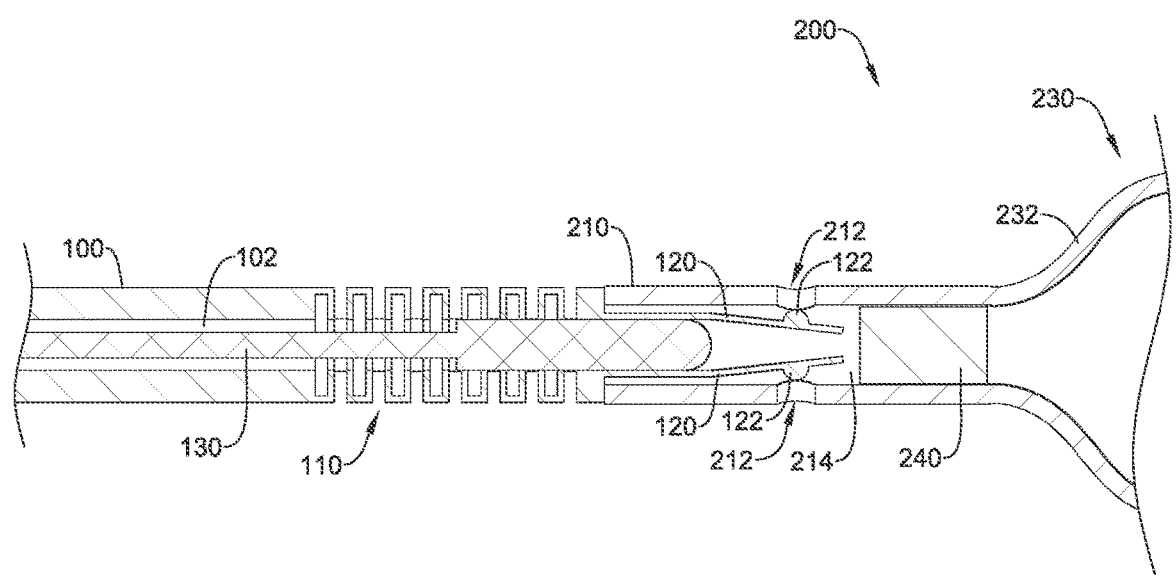

Turning now to FIGS. 8 and 9, which illustrate an alternative configuration of the attachment mechanism, the distal strain relief portion 110 includes a plurality of micromachined or laser cuts extending at an angle relative to the longitudinal axis of the elongate shaft 100 from an outer surface of the elongate shaft 100 through to the lumen 102 extending through the elongate shaft 100. As will be apparent to the skilled person, the distal strain relief portion 110 shown in FIG. 8 may also be used in conjunction with the attachment mechanism configurations of FIGS. 3 and 4. In some embodiments, the plurality of micromachined or laser cuts may be arranged at an oblique angle relative to the longitudinal axis of the elongate shaft 100. In some embodiments, the plurality of micromachined or laser cuts may be arranged substantially perpendicular to the longitudinal axis of the elongate shaft 100. The distal strain relief portion 110 having the plurality of micromachined or laser cuts may be optionally included in any of the disclosed and/or alternative configurations of the elongate shaft 100 described herein. In some embodiments, other methods of forming the plurality of micromachined or laser cuts may be employed, including but not limited to, electro discharge machining (EDM), chemical reaction and/or dissolution, saw cutting, stamping, injection molding, etc.

Additionally, in some embodiments, the proximal tubular mounting portion 210 may lack the ridge 216 and may alternatively include a plurality of apertures 212 extending from an outer surface of the proximal tubular mounting portion 210 through to the lumen 214 extending through the proximal tubular mounting portion 210, as seen in FIG. 8 for example. The plurality of apertures 212 may be configured to engage the plurality of retaining arms 120 when the release wire 130 is in the distal engagement position. In some embodiments, each of the protrusions 122 of the plurality of retaining arms 120 engages one of the plurality of apertures 212 of the proximal tubular mounting portion 210 when the release wire 130 is in the distal engagement position. When the release wire 130 is in the proximal released position, the plurality of retaining arms 120 may deflect radially inward and the protrusions 122 may disengage from the plurality of apertures 212 of the proximal tubular mounting portion 210, as seen in FIG. 9. In some embodiments, when the release wire 130 is in the proximal released position, the plurality of retaining arms 120 may be biased and/or self-biased radially inward and the protrusions 122 may thereby disengage from the plurality of apertures 212 of the proximal tubular mounting portion 210. In the configuration illustrated in FIGS. 8 and 9, the protrusions 122 may be formed as rounded buttons or knobs extending radially outward from the outer surface of the plurality of retaining arms 120. The plurality of apertures 212 may have a corresponding shape configured to complement and/or engage with the protrusions 122 of the plurality of retaining arms 120.

Figure 10:
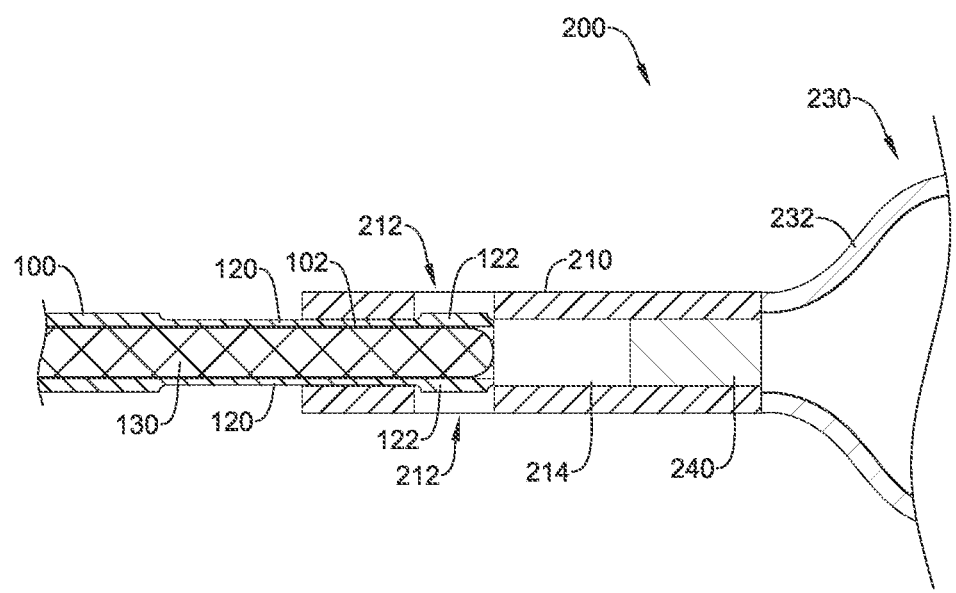
FIGS. 10-11 illustrate an alternative attachment mechanism of the occlusive medical device system.
Figure 11:
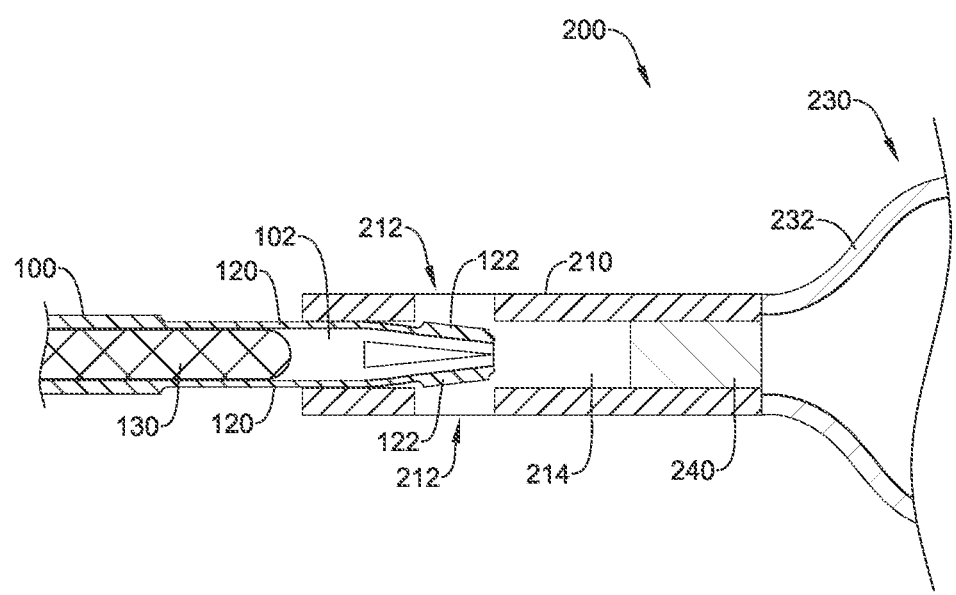

In an alternative configuration illustrated in FIGS. 10 and 11, the protrusions 122 of the plurality of retaining arms 120 may be formed as rectilinear and/or elongated protuberances having a longitudinal dimension arranged generally parallel to the longitudinal axis of the elongate shaft 100. Similar to the configuration of FIGS. 8 and 9, the proximal tubular mounting portion 210 may include a plurality of apertures 212 extending from an outer surface of the proximal tubular mounting portion 210 through to the lumen 214 extending through the proximal tubular mounting portion 210, as seen in FIG. 10 for example. The plurality of apertures 212 may be configured to engage the plurality of retaining arms 120 when the release wire 130 is in the distal engagement position. In some embodiments, each of the protrusions 122 of the plurality of retaining arms 120 engages one of the plurality of apertures 212 of the proximal tubular mounting portion 210 when the release wire 130 is in the distal engagement position. When the release wire 130 is in the proximal released position, the plurality of retaining arms 120 may deflect radially inward and the protrusions 122 may disengage from the plurality of apertures 212 of the proximal tubular mounting portion 210, as seen in FIG. 11.

Figure 12:
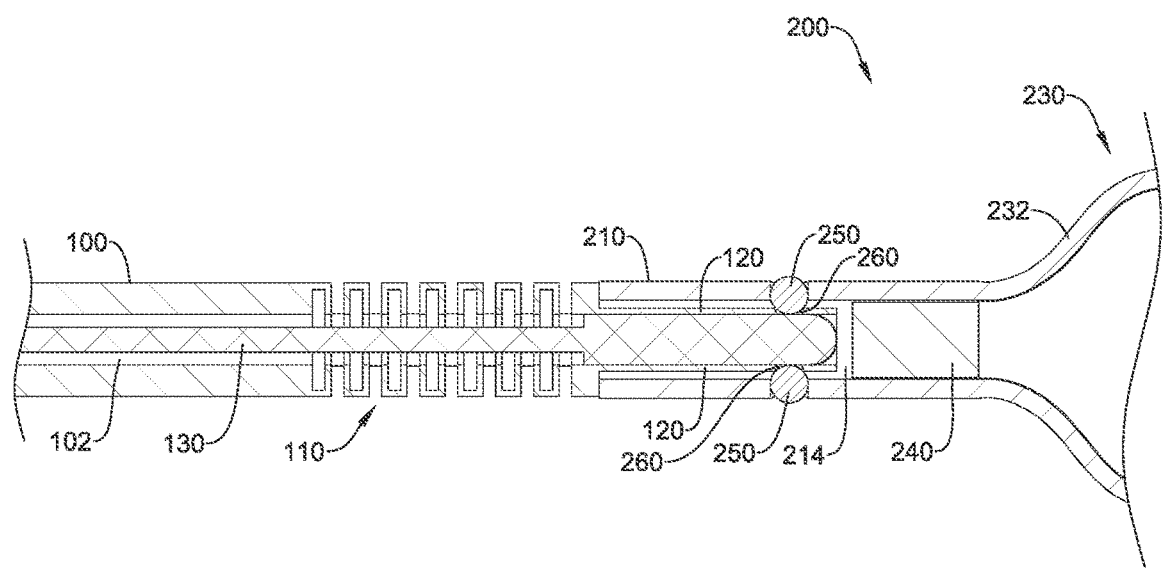
FIGS. 12-13 illustrate an alternative attachment mechanism of the occlusive medical device system.
Figure 13:
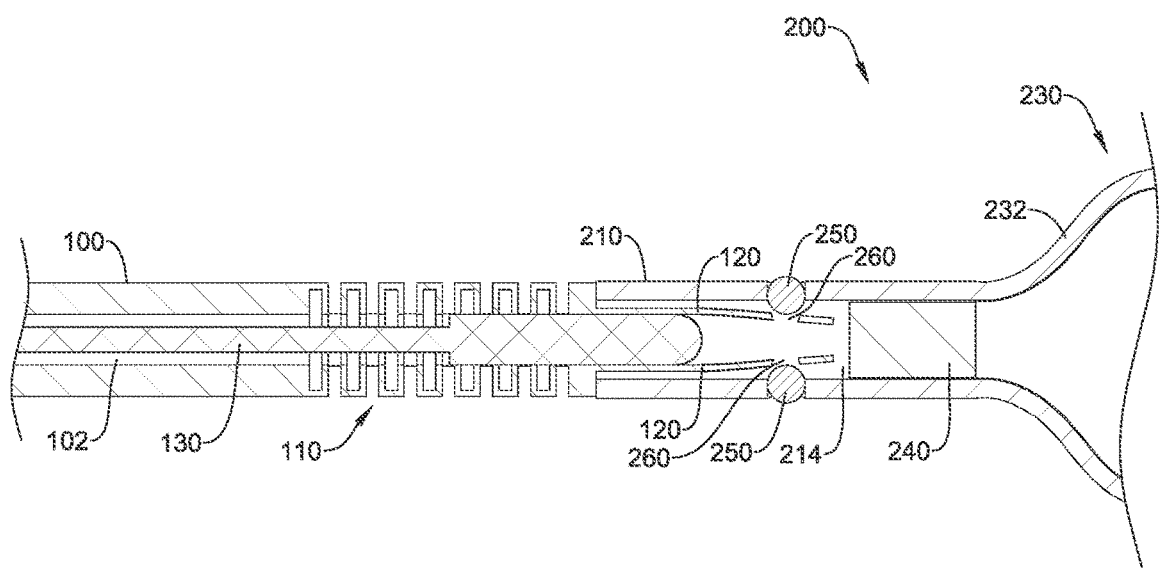

In another alternative configuration, the proximal tubular mounting portion 210 may include a plurality of protrusions 250 extending radially inward into the lumen 214 extending longitudinally through the proximal tubular mounting portion 210, as seen in FIG. 12. In some embodiments, the plurality of protrusions 250 may be formed as distinct, individual protrusions (e.g., balls, beads, rings, beaded rings, etc.) fixedly secured within openings extending through a side wall of the proximal tubular mounting portion 210. In some embodiments, the plurality of protrusions 250 may be integrally formed with the proximal tubular mounting portion 210. In the configuration shown in FIG. 12, each of the plurality of retaining arms 120 of the elongate shaft 100 may include an aperture 260 (collectively, a plurality of apertures) configured to engage one of the plurality of protrusions 250 when the release wire is in the distal engagement position. Function and operation of the occlusive medical device system may be similar to that described above and/or herein. When the release wire 130 is in the proximal released position, the plurality of retaining arms 120 may deflect radially inward and the apertures and/or the plurality of apertures 260 may disengage from the plurality of protrusions 250 of the proximal tubular mounting portion 210, as seen in FIG. 13.

In another alternative configuration, the arrangement(s) described above may be inverted, wherein the features of the distal end of the elongate shaft 100 (e.g., the plurality of retaining arms 120, the protrusion(s) 122, etc.) may be disposed on and/or be formed with a proximal end of the occlusive medical device 200, and the features of the proximal tubular mounting portion 210 (e.g., the lumen 214, the ridge 216, the tubular ring 218, the proximal aperture 220, the plurality of apertures 212, etc.) may be disposed on and/or be formed with a distal end of the elongate shaft 100. Other functionality may remain substantially the same as described above, with the plurality of retaining arms (now of the occlusive medical device) extending into the proximal tubular mounting portion (now of the elongate shaft), and the release wire 130 urging the plurality of retaining arms into releasable engagement with the proximal tubular mounting portion in the distal engagement position. Proximal translation of the release wire from the distal engagement position to the proximal release position may permit the plurality of retaining arms to disengage from the proximal tubular mounting portion and release the occlusive medical device from the elongate shaft.

Figure 14:
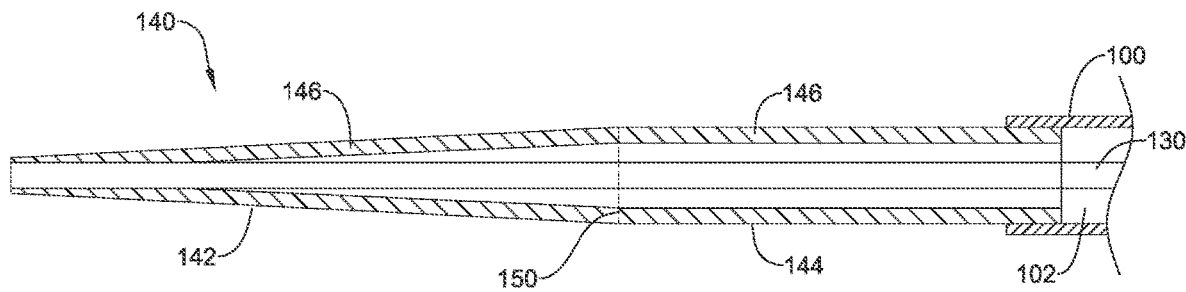
FIGS. 14-15 illustrate partial cut-away views of an example securement member.
Figure 15:
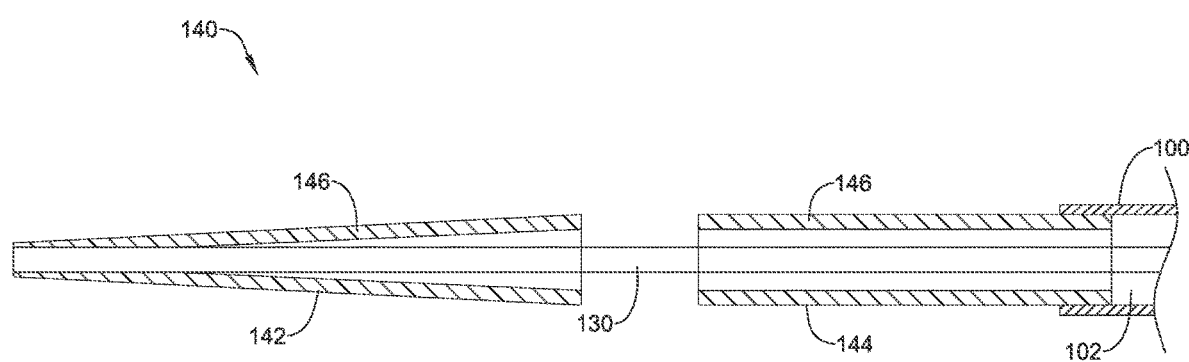

In some embodiments, the occlusive medical device system may include a securement member 140 fixedly attached to and/or extending proximally from a proximal end of the elongate shaft 100, and fixedly attached to a proximal end of the release wire 130. The securement member 140 may include a proximal portion 142, a distal portion 144, and a wall 146 (as seen in FIGS. 14 and 15, for example) extending from a proximal end of the securement member 140 to a distal end of the securement member 140. In at least some embodiments, the proximal portion 142 of the securement member 140 may be integrally formed with the distal portion 144 of the securement member 140 as a single unitary structure. Some suitable but non-limiting materials for the securement member 140, for example metallic materials, polymer materials, composite materials, etc., are described below.

In some embodiments, the proximal portion 142 of the securement member 140 may be configured to disengage from the distal portion 144 of the securement member 140. The proximal portion 142 of the securement member 140 may be fixedly attached to the proximal end of the release wire 130. The distal portion 144 of the securement member 140 may be fixedly attached to the proximal end of the elongate shaft 100. In at least some embodiments, an outer surface of the distal portion 144 of the securement member 140 may be fixedly attached to an inner surface of the elongate shaft 100 (e.g., a surface defining the lumen 102). Alternatively, in some embodiments, an inner surface of the distal portion 144 of the securement member 140 may be fixedly attached to an outer surface of the elongate shaft 100. In some embodiments, the proximal portion 142 of the securement member 140 may be releasably secured to and/or configured to disengage from the distal portion 144 of the securement member 140 at a joint 150. In some embodiments, the joint 150 may be a perforation, a dissimilar polymer joint, a frangible link, or other releasable securement feature formed in the wall 146 of the securement member 140.

In at least some embodiments, the securement member 140 may prevent axial translation of the release wire 130 relative to the elongate shaft 100 and/or the occlusive medical device 200 prior to disengagement of the proximal portion 142 of the securement member 140 from the distal portion 144 of the securement member 140. Disengaging the proximal portion 142 of the securement member 140 from the distal portion 144 of the securement member 140 may permit the release wire 130 to axially translate relative to the distal portion 144 of the securement member 140 and/or the elongate shaft 100. In other words, the wall 146 of the distal portion 144 of the securement member 140 may define a lumen, as seen in FIGS. 14 and 15 for example, wherein the release wire 130 is slidably disposed within the lumen of the distal portion 144 of the securement member 140. Upon disengagement of the proximal portion 142 of the securement member 140 from the distal portion 144 of the securement member 140, as seen in FIG. 15, axial translation of the proximal portion 142 relative to the distal portion 144 of the securement member 140 and/or the elongate shaft 100 may translate the release wire 130 relative to the elongate shaft 100 and/or the distal portion 144 of the securement member 140 to release the occlusive medical device 200 from the distal end of the elongate shaft 100, as explained herein.

The release wire 130, in the distal engagement position, urges the plurality of retaining arms 120 into releasable engagement with the proximal tubular mounting portion 210 of the occlusive medical device 200 when the proximal portion 142 of the securement member 140 is engaged with the distal portion 144 of the securement member 140. For example, when the proximal portion 142 of the securement member 140 is disengaged and/or separated from the distal portion 144 of the securement member 140, as seen in FIG. 15, the release wire 130 is translated in a proximal direction relative to the elongate shaft 100 to the proximal released position, thereby permitting the plurality of retaining arms 120 to deflect radially inward and disengage from the proximal tubular mounting portion 210, as described above. In some embodiments, the release wire 130 may be slidably disposed within the distal portion 144 of the securement member 140, the elongate shaft 100, the lumen 102, the plurality of retaining arms 120, and at least a portion of the proximal tubular mounting portion 210 and/or the lumen 214.

In use, the elongate shaft 100 may have sufficient length to reach from the target site or area of interest to a position outside of the patient where the occlusive medical device system may be manipulated by an operator (e.g., clinician, physician, user, etc.). The operator of the occlusive medical device system may then place a first hand on the distal portion 144 of the securement member 140 and a second hand on the proximal portion 142 of the securement member 140. The proximal portion 142 of the securement member 140 may be configured to disengage from the distal portion 144 of the securement member 140 at a location proximal of the delivery sheath 50. In at least some embodiments, the proximal portion 142 of the securement member 140 may be disengaged from the distal portion 144 of the securement member 140 by bending, twisting, and/or pulling the proximal portion 142 of the securement member 140 relative to the distal portion 144 of the securement member 140. In some embodiments, disengaging the proximal portion 142 of the securement member 140 from the distal portion 144 of the securement member 140 may include moving the proximal portion 142 of the securement member 140 relative to the distal portion 144 of the securement member 140 to separate the proximal portion 142 of the securement member 140 from the distal portion 144 of the securement member 140. In some embodiments, disengaging the proximal portion 142 of the securement member 140 from the distal portion 144 of the securement member 140 may include using an external device (e.g., a torque device, an external handle, etc.) to move the proximal portion 142 of the securement member 140 relative to the distal portion 144 of the securement member 140.

In some embodiments, the joint 150 may include a series of apertures (e.g., perforation) extending through the wall 146 of the securement member 140. In some embodiments, the joint 150 may extend circumferentially about an entire circumference of the wall 146 of the securement member 140. In some embodiments, the joint 150 may extend partially and/or intermittently about the entire circumference of the wall 146 of the securement member 140. Additionally, while the joint 150 is illustrated in FIGS. 14 and 15 as being generally oriented and/or positioned within a plane perpendicular to a longitudinal axis of the securement member 140, other orientations and/or positioning may be used. For example, in some embodiments, the joint 150 may be oriented and/or positioned within or along a plane at an oblique angle to the longitudinal axis of the securement member 140. Other, for example non-planar, configurations are also possible. The proximal portion 142 of the securement member 140 is disposed proximal of the joint 150 and the distal portion 144 of the securement member 140 is disposed distal of the joint 150. As mentioned above, the proximal portion 142 of the securement member 140 may be releasably secured to and/or configured to disengage from the distal portion 144 of the securement member 140 at the joint 150 formed in the wall 146 of the securement member 140.

The materials that can be used for the various components of the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc. (and/or other systems or components disclosed herein) and the various elements thereof disclosed herein may include those commonly associated with medical devices. For simplicity purposes, the following discussion makes reference to the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc. However, this is not intended to limit the devices and methods described herein, as the discussion may be applied to other elements, members, components, or devices disclosed herein, such as, but not limited to, the distal strain relief portion 110, the plurality of retaining arms 120, the protrusions 122, the ridge 216, the tubular ring 218, etc. and/or elements or components thereof.

In some embodiments, the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc. to achieve the same result.

In some embodiments, a degree of Magnetic Resonance Imaging (MM) compatibility is imparted into the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc. For example, the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the radiopaque insert 240, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the occlusive membrane 234, the radiopaque insert 240, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive medical device system, the delivery sheath 50, the elongate shaft 100, the release wire 130, the securement member 140, the occlusive medical device 200, the proximal tubular mounting portion 210, the expandable occlusive element 230, and/or the support frame 232, the occlusive membrane 234, the radiopaque insert 240, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An occlusive medical device system, comprising:
an elongate shaft having a proximal end, a distal strain relief portion, and a lumen extending longitudinally through the elongate shaft, the elongate shaft further comprising a plurality of retaining arms extending distally from the distal strain relief portion;
an occlusive medical device configured to occlude fluid flow through a vessel lumen, the occlusive medical device including a proximal mounting portion fixed to an expandable occlusive element;
a release wire disposed within the lumen of the elongate shaft and axially translatable between a distal engagement position and a proximal released position;
wherein the plurality of retaining arms extend into the proximal mounting portion;
wherein the release wire is configured to engage the plurality of retaining arms in the distal engagement position, thereby urging the plurality of retaining arms radially outward into releasable engagement with the proximal mounting portion of the occlusive medical device;
wherein when the release wire is in the proximal released position, the plurality of retaining arms is deflectable radially inward to disengage from the proximal mounting portion; and
a securement member having a proximal portion fixedly attached to a proximal end of the release wire and a distal portion fixedly attached to a proximal end of the elongate shaft;
wherein the securement member is configured to prevent axial translation of the release wire relative to the elongate shaft prior to disengagement of the proximal portion of the securement member from the distal portion of the securement member and permit axial translation of the release wire relative to the elongate shaft after disengagement of the proximal portion of the securement member from the distal portion of the securement member.

2. The occlusive medical device system of claim 1, wherein the distal strain relief portion includes a plurality of micromachined or laser cuts extending at an angle to a longitudinal axis of the elongate shaft from an outer surface of the elongate shaft through to the lumen extending through the elongate shaft.

3. The occlusive medical device system of claim 2, wherein the plurality of micromachined or laser cuts extend perpendicular to the longitudinal axis of the elongate shaft.

4. The occlusive medical device system of claim 1, wherein the proximal mounting portion includes a plurality of apertures configured to engage the plurality of retaining arms when the release wire is in the distal engagement position.

5. The occlusive medical device system of claim 4, wherein each of the plurality of retaining arms includes a protrusion extending radially outward from an outer surface of the retaining arm.

6. The occlusive medical device system of claim 5, wherein each of the protrusions of the plurality of retaining arms engages one of the plurality of apertures of the proximal mounting portion when the release wire is in the distal engagement position.

7. An occlusive medical device system, comprising:
an elongate shaft having a proximal end, a distal strain relief portion, and a lumen extending longitudinally through the elongate shaft, the elongate shaft further comprising a plurality of retaining arms extending distally from the distal strain relief portion, each retaining arm having a protrusion proximate a distal end thereof and extending radially outward from an outwardly-facing surface of the retaining arm;
an occlusive medical device configured to occlude fluid flow through a vessel lumen, the occlusive medical device including a proximal tubular mounting portion fixed to an expandable occlusive element, the proximal tubular mounting portion including a lumen extending longitudinally through the proximal tubular mounting portion and a ridge extending radially inward from an inwardly-facing surface of the proximal tubular mounting portion proximate a proximal end of the proximal tubular mounting portion;
a release wire disposed within the lumen of the elongate shaft and axially translatable between a distal engagement position and a proximal released position;
wherein the plurality of retaining arms extend into the proximal tubular mounting portion;
wherein the release wire is configured to engage the plurality of retaining arms in the distal engagement position, thereby urging the plurality of retaining arms radially outward such that proximal axial translation of the elongate shaft relative to the proximal tubular mounting portion is prevented;
wherein when the release wire is in the proximal released position, the plurality of retaining arms is deflectable radially inward such that proximal axial translation of the elongate shaft relative to the proximal tubular mounting portion is permitted; and
a securement member having a proximal portion fixedly attached to a proximal end of the release wire and a distal portion fixedly attached to a proximal end of the elongate shaft;
wherein the securement member is configured to prevent axial translation of the release wire relative to the elongate shaft prior to disengagement of the proximal portion of the securement member from the distal portion of the securement member and permit axial translation of the release wire relative to the elongate shaft after disengagement of the proximal portion of the securement member from the distal portion of the securement member.

8. The occlusive medical device system of claim 7, wherein the ridge is integrally formed with the proximal tubular mounting portion.

9. The occlusive medical device system of claim 7, wherein the ridge is formed as a part of a tubular ring fixedly attached to a proximal end of the proximal tubular mounting portion.

10. The occlusive medical device system of claim 7, wherein the ridge defines a proximal aperture having a diameter less than a diameter of the lumen of the proximal tubular mounting portion.

11. The occlusive medical device system of claim 10, wherein the diameter of the proximal aperture is less than a maximum outer extent of the protrusions of the plurality of retaining arms when the release wire is in the distal engagement position.

12. The occlusive medical device system of claim 7, wherein the occlusive medical device includes a radiopaque insert disposed within the lumen of the proximal tubular mounting portion.

13. The occlusive medical device system of claim 12, wherein the elongate shaft is axially slidable within the proximal tubular mounting portion.

14. The occlusive medical device system of claim 13, wherein advancing the elongate shaft distally urges the distal ends of the plurality of retaining arms into contact with the radiopaque insert.

15. The occlusive medical device system of claim 13, wherein when the release wire is in the distal engagement position, withdrawing the elongate shaft proximally urges the protrusions of the plurality of retaining arms into contact with the ridge.

16. An occlusive medical device system, comprising:
an elongate shaft having a proximal end, a distal strain relief portion, and a lumen extending longitudinally through the elongate shaft, the elongate shaft further comprising a plurality of retaining arms extending distally from the distal strain relief portion;
an occlusive medical device configured to occlude fluid flow through a vessel lumen, the occlusive medical device including a proximal mounting portion fixed to an expandable occlusive element comprising a support frame and an occlusive membrane attached to the support frame;
a release wire disposed within the lumen of the elongate shaft and axially translatable between a distal engagement position and a proximal released position;
wherein the plurality of retaining arms extend into the proximal mounting portion;
wherein the release wire is configured to engage the plurality of retaining arms in the distal engagement position, thereby urging the plurality of retaining arms radially outward into releasable engagement with the proximal mounting portion of the occlusive medical device;
wherein when the release wire is in the proximal released position, the plurality of retaining arms is deflectable radially inward to disengage from the proximal mounting portion; and
a securement member having a proximal portion fixedly attached to a proximal end of the release wire and a distal portion fixedly attached to a proximal end of the elongate shaft;
wherein the securement member is configured to prevent axial translation of the release wire relative to the elongate shaft prior to disengagement of the proximal portion of the securement member from the distal portion of the securement member and permit axial translation of the release wire relative to the elongate shaft after disengagement of the proximal portion of the securement member from the distal portion of the securement member.

17. The occlusive medical device system of claim 16, wherein the occlusive medical device includes a lumen extending longitudinally through the proximal mounting portion and a radiopaque marker fixedly secured within a distal end of the lumen extending longitudinally through the proximal mounting portion.

18. The occlusive medical device system of claim 17, wherein the proximal mounting portion includes a plurality of protrusions extending radially inward into the lumen extending longitudinally through the proximal mounting portion.

19. The occlusive medical device system of claim 18, wherein each of the plurality of retaining arms includes an aperture configured to engage one of the plurality of protrusions when the release wire is in the distal engagement position.

* * * * *